US00PP23681P2

(12) United States Plant Patent
Deuter

(10) Patent No.: US PP23,681 P2
(45) Date of Patent: Jun. 18, 2013

(54) ***MISCANTHUS* PLANT NAMED 'MBS 7003'**

(50) Latin Name: ***Miscanthus* sp.**
Varietal Denomination: MBS 7003

(75) Inventor: Martin Deuter, Wanzleben (DE)

(73) Assignee: Mendel Biotechnology, Inc., Hayward, CA (US)

( * ) Notice: Subject to any disclaimer, the term of this patent is extended or adjusted under 35 U.S.C. 154(b) by 29 days.

(21) Appl. No.: 13/067,963

(22) Filed: Jul. 12, 2011

Related U.S. Application Data

(63) Continuation-in-part of application No. 12/584,496, filed on Sep. 4, 2009, now Pat. No. Plant 22,127, which is a continuation-in-part of application No. 12/387,444, filed on May 1, 2009, now Pat. No. Plant 22,033, and a continuation-in-part of application No. 12/387,429, filed on May 1, 2009, now Pat. No. Plant 22,047, and a continuation-in-part of application No. 12/387,437, filed on May 1, 2009, now abandoned.

(60) Provisional application No. 61/050,162, filed on May 2, 2008.

(51) Int. Cl.
*A01H 5/00* (2006.01)

(52) U.S. Cl.
USPC ..... Plt./384

(58) Field of Classification Search
USPC ..... Plt./384
See application file for complete search history.

(56) References Cited

U.S. PATENT DOCUMENTS

| | | | |
|---|---|---|---|
| PP13,008 | P2 | 9/2002 | Walsh |
| PP15,193 | P2 | 9/2004 | Smith et al. |
| PP16,197 | P2 | 1/2006 | Weiskott |
| PP18,161 | P2 | 10/2007 | Probst |
| PP22,033 | P2 | 7/2011 | Deuter |
| PP22,047 | P2 | 7/2011 | Deuter |
| PP22,127 | P2 | 9/2011 | Deuter |

OTHER PUBLICATIONS

U.S. Appl. No. 12/584,496, filed Sep. 4, 2009, Deuter.
U.S. Appl. No. 12/387,444, filed May 1, 2009, Deuter.
U.S. Appl. No. 12/387,429, filed May 1, 2009, Deuter.
U.S. Appl. No. 12/387,437, filed May 1, 2009, Deuter.
U.S. Appl. No. 12/387,437, Deuter.

*Primary Examiner* — Susan McCormick Ewoldt
(74) *Attorney, Agent, or Firm* — Cooley LLP

(57) ABSTRACT

A new and distinct cultivar of *Miscanthus* plant named 'MBS 7003', generally characterized by its vigorous growth rate, top leaf height, green-colored leaves, high biomass yield and high tiller density.

2 Drawing Sheets

Latin name of genus: *Miscanthus* sp.
Varietal denomination: 'MBS 7003', or 'Columbia'.

BACKGROUND

The present disclosure relates to a new and distinct cultivar of hybrid *Miscanthus* originated as a cross from *Miscanthus sacchariflorus* (♀, 4n) and *M. sinensis* (♂, 2n) plants, and will be referred to hereafter by its cultivar name, 'MBS 7003'. 'MBS 7003' represents a new cultivar of *Miscanthus* species, a perennial grass which is grown for biomass production, building materials, livestock bedding, landscape use and ornamental value.

The new cultivar MBS 7003 is a fertile *M.×giganteus* (4×) plant. It is unique to other *M.×gigateus* cultivars in that in can be propagated by rhizomes, stem, and from seed if pollinated with a different compatible genotype. Details describing its phenotypic and performance identity are indicated herein.

The invention described in this application was derived through the process of botanical plant breeding techniques, phenotypic and genotypic identification, and stability of performance compared to other *M.×giganteus* type cultivars. Initial breeding work was done at Klein Wanzleben, Germany utilizing the greenhouse for crossing and selection, with subsequent field evaluation. Selection on the clonal propagated genotype was made at Klein-Wanzleben. Additional evaluation occurred in the US upon receiving plant material following successful APHIS regulated importation quarantine process.

'MBS 7003', also known as 'Columbia', was selected for its vigorous growth from a selection field which was established from seedlings. The seedlings were obtained from seeds of a polycross of *Miscanthus sacchariflorus* (♀, 4n) and *M. sinensis* plants (♂, 2n). 'MBS 7003' was generated by crossing a single large-stemmed *M. sacchariflorus* genotype from Japan (accession No.: 93M0005064, ploidy: 4×) as a female parent with a population of 15 *M. sinensis* plants a pollen donors (accession Nos.: 93m0146002, 92M0179020, 92M1079017, 93M0147009, 92M0179016, 93m0146012, 93M0144001, 93m0146017, 92m0086, 92m0179015, 93m0146001, 93M0084, 93m0006005, 93M0006003, and 93m0007212; ploidy: 2×). From this cross, 158 seedlings were obtained and planted in a field. Based on field observations, a tetraploid variety having high biomass was selected and designated as 'MBS 7003'.

The commercial comparison to 'MBS 7003' is *M.×giganteus* cv. 'Illinois'. 'Illinois' was derived from a similar interspecific cross using different parental genotypes between *Miscanthus sacchariflorus* (4×) and *M. sinensis* (2×) resulting in a sterile clone plant selection that is available to the public.

'MBS 7003' is different from *Miscanthus* variety 'MBS 7001' ('Nagara') disclosed in U.S. Plant Pat. No. 22,033.

'MBS 7003' of the present application is 100% fertile, and is approximately 95% to 100% self incompatible and 95% to 100% cross compatible. *Miscanthus* variety 'MBS 7001' ('Nagara') is approximately 98% to 100% sterile genotype, and is almost completely self and cross incompatible. Therefore, 'MBS 7001' rarely produces seed. In contrast, 'MBS 7003' produces significantly higher amounts of seed.

Fertile 'MBS 7003' is different from the commercially available *M.×giganteus* cv. 'Illinois' is considered to be a 100% sterile genotype, that is, 'Illinois' is completely self- and cross-incompatible.

'MBS 7003' is also different from *Miscanthus* variety 'MBS 7002' ('Lake Erie') disclosed in U.S. Plant Pat. No. 22,047. 'MBS 7003' is shorter in plant height both during the growing season and at seasonal maturity than 'MBS 7002'.

'MBS 7003' is a cross compatible sibling of the *Miscanthus* variety 'MBS 1001' disclosed in the co-pending U.S. Plant patent application Ser. No. 13/067,964. 'MBS 7003' is different from 'MBS 1001' in that 'MBS 7003' has greater vegetative transplanting vigor, and is significantly shorter than 'MBS 1001'.

'MBS 7003' is also different from *Miscanthus* variety 'MBS 1002' ('MDL 1002') disclosed in U.S. Plant Pat. No. 22,127. 'MBS 1002' is taller, is later flowering and matures later than 'MBS 7003'. 'MBS 1002' has higher seedling vigor than 'MBS 7003' upon transplanting, and during spring greenup MBS 1002 has slightly better cold tolerance than 'MBS 7003'.

'MBS 7003' flowers earlier than 'MBS 7002' (see U.S. Pat. No. 22,047), 'MBS 1001' (see U.S. patent application Ser. No. 13/067,964 filed Jul. 12, 2011), and 'MBS 1002' (see U.S. Pat. No. 22,127).

'MBS 7002', 'MBS 7003', and 'MBS 1002' are siblings and recombine very well in crossing.

'MBS 7003' was established asexually from sterile rhizome buds in Klein-Wanzleben, Germany by the inventor. The shoot material was propagated on rooting media and the rooted plantlets were planted into pots in the greenhouse. The plants were planted into the field after one cold period. The characteristics of this cultivar have been determined to be stable and are reproduced true to type in successive generations.

SUMMARY

'MBS 7003' (a.k.a. 'Columbia')

The following traits have been repeatedly observed and represent the basic characteristics of the new cultivar. The new cultivar 'MBS 7003' has not been observed under all possible environmental conditions. The phenotype may vary somewhat with variations in temperature, day length, light intensity, soil types, and water and fertility levels without, however, any variance in genotype.

The following traits in combination distinguish this *Miscanthus* hybrid from *Miscanthus×giganteus* cv. 'Illinois' and ornamental *M. sinensis* forms. Plants for the botanical measurements in the present application are two to three-year-old plants. These plants would be considered as mature plants.

1. Vigorous growth
2. Top leaf height about 2.7 meters
3. Green leaves, no colored stripes are present
4. High biomass yield (about 20-30 metric tons per hectare, equals to 9-13 U.S. tons per acre)
5. High tiller density 'MBS 7003' can be distinguished from the *Miscanthus* cultivars 'Strictus' (not patented, a.k.a 'Porcupine grass'), 'Super Stripe' (U.S. Plant Pat. No. 18,161), 'Gold Bar' (U.S. Plant Pat. No. 15,193), 'Little Zebra' (U.S. Plant Pat. No. 13,008), and 'Mysterious Maiden' (U.S. Plant Pat. No. 16,197) in that 'MBS 7003' has no stripes or colored bands on its leaves.

In side by side comparisons conducted at Klein-Wanzleben, Germany, 'MBS 7003' is more vigorous than either of its parent plants and produces more biomass than either parent. 'MBS 7003' has taller culms but demonstrates less lodging; hence, it has stronger culms than the parent phenotypes. The leaves stay longer on the cutin compared to *M.×giganteus* cv. 'Illinois', and therefore, overall leaf loss during the winter is less than *M.×giganteus* cv. 'Illinois'.

'MBS 7003' can be propagated by rhizomes, from meristem or nodes. This further distinguishes 'MBS 7003' from *M. sinensis* in that *M. sinensis* cannot be propagated by nodes. 'MBS 7003' develops inflorescences and viable seed under optimal growing conditions.

BRIEF DESCRIPTION OF THE DRAWINGS

The accompanying color photographs illustrate the overall appearance and distinct characteristics of the new *Miscanthus* cultivar 'MBS 7003'.

DETAILED BOTANICAL DESCRIPTION OF THE PLANT

Figure 1:
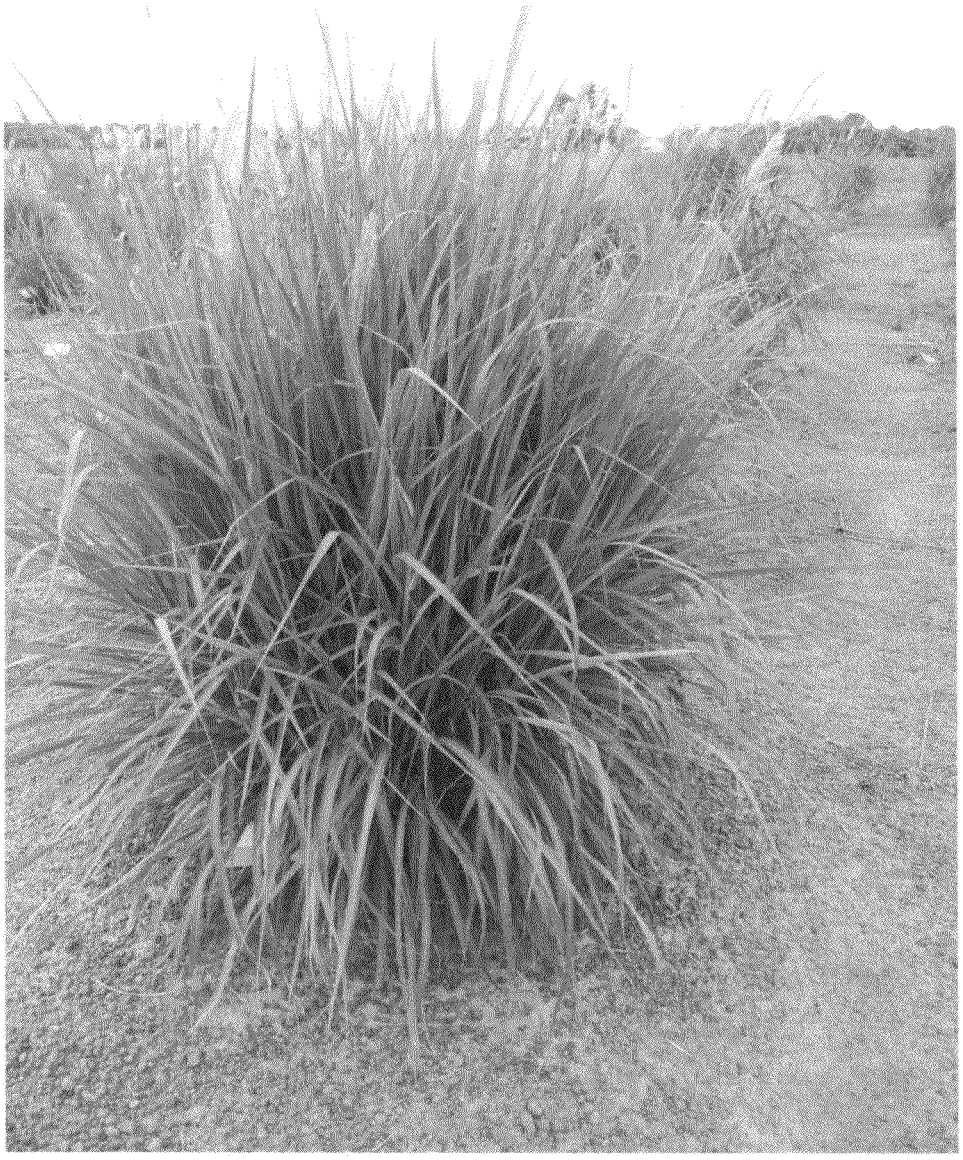
FIG. 1 depicts 'MBS 7003' ('Columbia') in mid summer of $2^{nd}$ year growth at Tifton, Ga. The picture represents biomass stature from re-growth after winter biomass harvest via removal of all dormant biomass about 8" above ground surface. The picture was taken in late June, and the plants were grown under dry land conditions. The plant in FIG. 1 has a maturity height of approximately 1.5 meters.
Figure 2:
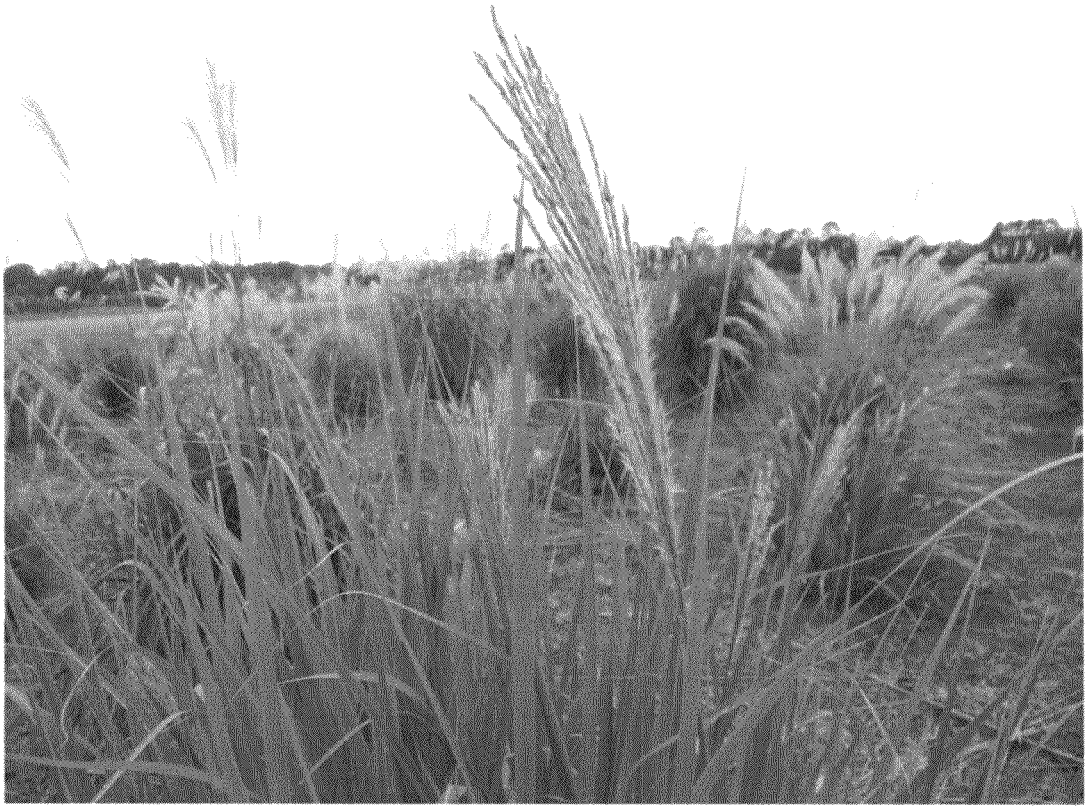
FIG. 2 depicts 'MBS 7003' ('Columbia') with panicle emergence. The picture was taken during mid summer, second year growth, under dry-land conditions at Tifton, Ga.

'MBS 7003' has not been observed under all possible environmental conditions, and the phenotype may vary significantly with variations in environment. The following observations, measurements, and comparisons describe this plant as grown at Klein-Wanzleben, Germany, when grown in the field, unless otherwise noted. Many observations were recorded during the plant's dormant season (April 2008) and during the 2007 and 2008 growing season unless otherwise noted such as in the yield data provided, and descriptive data performed at Tifton, Ga. The color determination is in accordance with The 1995 R.H.S. Colour Chart of The Royal Horticultural Society, London, England, except where general color terms of ordinary dictionary significance are used. Plants for the botanical measurements in the present application are two and three-year old plants. These plants would be considered mature plants.

Botanical classification: 'MBS 7003' is a fertile hybrid of a cross from *Miscanthus sinensis* and *Miscanthus sacchariflorus*.

Common name: Maiden grass.

Parentage: Polycross of *M. sacchariflorus* and several *M. sinensis*.

General description:

*Blooming period*.—'MBS 7003' may bloom in early to mid-fall in the Southern and Central US. Blooms are retained over the winter, and are slow to senesce and drop.

*Plant habit*.—Herbaceous, tuft forming, biomass grass with upright culms. 17-20 leaves per culm.

*Height*.—Top leaf height ~2.2 meters at 3 year maturity.

*Hardiness*.—Productive growth in Klein-Wanzleben (north central), Germany; Ontario, Canada; latitudes Southeastern, Mid-Atlantic and South Central regions, Northern and Midwest US.

*Culture*.—Best in sandy loam, well-drained soil, higher yields at higher soil fertility.

*Diseases and pests*.—In the United States, 'MBS 7003' has shown excellent resistance to lesser stem borer spp. when compared to the public variety *M.×giganteus* cv. 'Illinois' clone. Observations and confirmation on stem borer tolerance occurred during early stages within 2-8 weeks after planting of seedling material. This has been observed across at least 7 locations, particularly in the Southeastern US.

*Root description*.—Fibrous, well branched and dense. Fast-developing creeping rhizomes, with shoots arising about 5-10 cm from the base of the culms.

Growth and propagation:

*Vegetative propagation*.—By cutin division, in vitro culture., from rhizomes, meristem or axillary buds (nodes).

*Growth rate*.—Vigorous.

*Seed propagation*.—Next generation seed can be supplied as breeder's and foundation seed. Rapid germination, followed by slow growth and then rapid growth to maturity if planted in the Spring from the Midwest to Southeastern regions of the US.

The following descriptions are based on data from 2-3 year old plants, which are considered mature plants.

Culm (stem) description:

*General*.—Cylindrical, pithy, reed-like, erect, sheathed.

*Culm aspect*.—Rigid and held erect, none are cascading.

*Culm color* (*dormant season*).—Yellowish, lower internodes partly reddish. Midsummer color is yellow green (RHS 144B or 145C), lower internodes partly reddish orange (RHS 164B or 165B), and varies with intensity depending on location latitude, growing conditions, and time of observation.

*Culm size*.—Average about 8.4 mm in diameter, 2.2 m in height.

*Basal circumference*.—90 cm at two year maturity and 193 cm at 5 year plant maturity.

*Culm surface*.—Culm is covered with many hairs on the green leaf sheaths.

*Internode length*.—6 to 18 cm.

*Ligule*.—Membranous, about 4 mm (*M.×giganteus* cv. 'Illinois' is 2.5-3 mm), color reddish, RHS 145C, border RHS 59D, longest hair is 2 mm (*M.×giganteus* cv. 'Illinois' 1 mm), encircles the entire culm, inner surface is glabrous, hairs on the outer surface, long hairs are mainly on the side, hairs on the side are approximately 6 mm (*M.×giganteus* cv. 'Illinois' 4-5 mm).

Foliage description:

*Leaf shape*.—Linear.

*Leaf base*.—Sheathed.

*Leaf division*.—Simple.

*Leaf apex*.—Acuminate.

*Leaf aspect*.—Emerging leaves are erect; leaf blades are convex, leaf angle younger leaves 50°, leaf angle older leaves 5°, color-code RHS 141B for leaf upper surface and 141C for lower leaf surface.

*Leaf tip younger leaves*.—½ pendently, meaning approximately half of the leaf tip area if the younger leaves bends downward.

*Leaf venation*.—Parallel, upper surface concave, lower surface convex.

*Leaf margins*.—Entire, visible, sharp short bristles under the microscope.

*Leaf size*.—Up to 125 cm length, width: 2-3.5 cm.

*Leaf attachment*.—Sheathed.

*Leaf arrangement*.—Alternate, tapering.

*Leaf surface*.—Upper-light glossy, lower-matte, single hairs on some leaves on the lower surface.

*Leaf color* (*during growing season*).—Green, RHS 141B for upper leaf and RHS 141C for lower leaf, no stripes. No hairs on lower leaf surface.

Flower and reproductive organ description:

*General description*.—Compact, fan-shaped panicle generating from each culm in mid to late September, composed of numerous slender, silky aggregate racemes. Under extreme drought conditions and at southern US latitudes 'MBS 7003' will generate from maturing culms in early to mid-summer and continue until mid fall prior to fall senescence.

*Persistence of inflorescence*.—Panicles are persistent from fall through winter until they dehisce from culms.

*Fragrance*.—None.

*Panicle size*.—Average of 22 cm in length per raceme and ~31 cm in width.

*Angle of raceme*.—35° at maturity and pre-senescence.

*Panicle color*.—Varies from RHS 153B-172C. The intensity of these color grades depends on location and growing conditions. However, this color report indicates that RHS 172B would be early panicle appearance and RHS 153B is for more mature panicle appearance.

*Spikelet description*.—Spikelet in pairs.

*Spikelet size*.—About 5 mm in length and 1 mm in width (excluding hairs).

*Spikelet color*.—RHS 151B.

*Spikelet hairs*.—12 mm in length, RHS 158C in color.

*Awn size*.—1 mm.

Reproductive organ description:

*Androecium*.—Anthers; 3.5 mm in length and 0.5 mm in width, red in color, RHS 187C.

*Gynoecium*.—Stigma color is RHS 187A, red, 4 mm in length and 0.5 mm in width.

*Caryopsis*.—Produces fertile seeds.

'MBS 7003' Miscanthus has a small elliptical seed, which is a heavy anemochore with an average seed weight of 0.96 mg, a chamaephyte (buds permanently above ground) life form, with an annual seed production of 64-1200 seeds per plant depending upon pollen source availability. Healthy seeds are clear amber to dark brown RHS 167B-200A. Table 1 below indicates dry tons per acre, average basal circumference, average compression circumference, average culm diameter, and average culm length of 'MBS 7003', and flower maturity ratings compared to *M.×giganleus* cv. 'Illinois', and three sister lines (i.e. 'MBS 7002', 'MBS 1001', and 'MBS 1002') over several locations.

TABLE 1

Two-year yield and plant data for MBS cultivar performances for 'MBS 7002', 'MBS 7003', 'MBS 1001', and 'MBS 1002'.

| Material Name | Yield (dton/ac) | Rk | % Moisture | Basal Circumference (Bcirc) cm |
|---|---|---|---|---|
| 'MBS 1001' | 8.01 | 1 | 24.8 | 90.6 |
| 'MBS 7002' ('Lake Erie') | 7.90 | 2 | 24.8 | 86.3 |
| *M.* x *giganteus* cv. 'Illinois' | 7.71 | 3 | 23.2 | 114.4 |
| 'MBS 1002' | 7.34 | 4 | 25.6 | 88.5 |
| 'MBS 7003' ('Columbia') | 7.15 | 5 | 26.6 | 87.9 |
| Grand Mean | 5.67 | | 23.8 | 92.7 |
| Locs × Years | (6 × 2) 12* | | (6 × 2) 12 | (5 × 1) 5** |
| LSD(.05) | 0.81 | | 2.7 | 5.3 |
| CVErr | 13.3 | | 16.4 | 5.2 |
| CVExL | 28.4 | | 23.0 | 7.1 |

| Material Name | Compressed Circumference (CCirc) cm | Culm Diameter (CmD) mm | Culm Length (CmL) cm | Flower Maturity Rating |
|---|---|---|---|---|
| 'MBS 1001' | 31.1 | 8.6 | 248.5 | 3.0 |
| 'MBS 7002' ('Lake Erie') | 29.1 | 7.6 | 247.0 | 4.0 |
| *M.* x *giganteus* cv. 'Illinois' | 25.9 | 7.3 | 260.8 | 5.0 |
| 'MBS 1002' | 33.4 | 9.0 | 239.7 | 4.0 |
| 'MBS 7003' ('Columbia') | 32.5 | 8.4 | 213.5 | 2.0 |
| Grand Mean | 26.4 | 7.5 | 218.5 | 3.6 |
| Locs × Years | (6 × 1) 6*** | (6 × 1) 6 | (5 × 1) 5 | (6 × 1) 6 |
| LSD(.05) | 3.4 | 1.0 | 9.4 | 0.2 |
| CVErr | 13.1 | 13.8 | 3.9 | 7.8 |
| CVExL | 17.7 | 18.3 | 5.3 | 8.5 |

Grand Mean: Trial mean (Combined years and US locations)

Locs × Years: Number of years and US locations for derivation of statistical values.

CVErr: coefficient of variation for entire error term of analysis.

CVExL: coefficient of variation error-location effects.

*Refers to that the mean value was calculated based on data collected from 6 locations in two years, therefore 12 total observations were made.

**Refers to that the mean value was calculated based on data collected from 5 locations in one year, therefore 5 total observations were made.

***Refers to that the mean value was calculated based on data collected from 6 locations in one year, therefore 6 total observations were made.

For dry tons per acre feedstock performances over two years and six locations of mature *Miscanthus* plots, 'MBS 7003' was significantly less than sister line 'MBS 1001', but similar to the commercial *M.×giganteus* cv. 'Illinois', and sister lines 'MBS 7002' and 'MBS 1001'.

Over six locations in the second year of mature growth 'MBS 7003' had significantly smaller basal circumference than commercial *M.×giganteus* cv. 'Illinois', but was similar to its sister lines in comparison. However, 'MBS 7003' had significantly greater culm diameter than 'Illinois' over the same five locations.

'MBS 7003' is significantly shorter by measurement of culm length compared to all sister lines and commercial variety 'Illinois'.

Flower maturity ratings indicated 'MBS 7003' as being significantly earlier than its sister MBS lines and the commercial 'Illinois'.

Yield:

The average yield of 'MBS 7003' compared to *Miscanthus×giganteus* cv. 'Illinois' is provided below in Table 2. Although there was virtually no statistical significance between 'Illinois' and 'MBS 7003' for feedstock yield, the two locations demonstrated that 'MBS 7003' was consistently higher in yield than the commercially available variety.

TABLE 2

Average 2 year feedstock yield (dry tons/ac) in Canada*

| Material Name | Leamington | Elora | Entry Mean |
|---|---|---|---|
| 'MBS 7003' | 2.6 | 5.3 | 3.9 |
| *M* x *giganteus* cv. 'Illinois' | 1.7 | 4.5 | 3.1 |
| Location means | 2.4 | 6.1 | 4.3 |
| LSD 0.05 | 1.3 | 2.8 | 1.8 |

*Data from 2 year old mature plants

The invention claimed is:

1. A new and distinct cultivar of *Miscanthus* plant named 'MBS 7003' substantially as herein shown and described.

* * * * *